United States Patent
Koehn

(10) Patent No.: US 8,560,010 B2
(45) Date of Patent: Oct. 15, 2013

(54) CELL PHONE WITH BREATH ANALYZER

(76) Inventor: Wade Koehn, Boutte, LA (US)

( * ) Notice: Subject to any disclaimer, the term of this patent is extended or adjusted under 35 U.S.C. 154(b) by 574 days.

(21) Appl. No.: 12/491,351

(22) Filed: Jun. 25, 2009

(65) Prior Publication Data
US 2009/0325639 A1 Dec. 31, 2009

Related U.S. Application Data

(60) Provisional application No. 61/075,459, filed on Jun. 25, 2008.

(51) Int. Cl.
*H04M 1/00* (2006.01)

(52) U.S. Cl.
USPC ............... 455/556.1; 422/83; 422/84; 422/98

(58) Field of Classification Search
USPC ......... 455/556.1, 456.1; 422/84, 62, 68.1, 83, 422/88, 94, 98, 416
See application file for complete search history.

(56) References Cited

U.S. PATENT DOCUMENTS

| | | | | |
|---|---|---|---|---|
| 4,749,553 A * | 6/1988 | Lopez et al. | ..................... | 422/84 |
| 4,926,164 A * | 5/1990 | Porter et al. | ................... | 340/576 |
| 5,220,919 A * | 6/1993 | Phillips et al. | ................ | 600/345 |
| 5,668,304 A * | 9/1997 | Kelleter et al. | .............. | 73/31.05 |
| 6,167,746 B1 | 1/2001 | Gammenthaler | ........... | 73/19.01 |
| 6,336,354 B1 * | 1/2002 | Suzuki et al. | ................ | 73/31.05 |
| 6,726,636 B2 | 4/2004 | Der Ghazarian et al. | | |
| 6,858,182 B1 * | 2/2005 | Ito et al. | ........................ | 422/416 |
| 2002/0084130 A1 * | 7/2002 | Der Ghazarian et al. | ..... | 180/272 |
| 2002/0127145 A1 * | 9/2002 | Der Ghazarian et al. | ........ | 422/83 |
| 2003/0183437 A1 * | 10/2003 | Mendoza | ....................... | 180/272 |
| 2004/0081582 A1 * | 4/2004 | Brooke | .......................... | 422/62 |
| 2004/0138823 A1 * | 7/2004 | Gollar | ............................. | 702/19 |
| 2004/0213701 A1 * | 10/2004 | Hattori et al. | ................... | 422/98 |
| 2005/0053523 A1 * | 3/2005 | Brooke | ......................... | 422/68.1 |
| 2006/0009257 A1 * | 1/2006 | Ku | .............................. | 455/556.1 |
| 2006/0058697 A1 * | 3/2006 | Mochizuki et al. | ........... | 600/532 |
| 2006/0193749 A1 * | 8/2006 | Ghazarian et al. | .............. | 422/83 |
| 2006/0202842 A1 * | 9/2006 | Sofer | ............................ | 340/576 |
| 2006/0238362 A1 * | 10/2006 | Mobley et al. | ................ | 340/576 |
| 2006/0244461 A1 * | 11/2006 | Song et al. | .................... | 324/500 |
| 2007/0016092 A1 * | 1/2007 | Shaw et al. | ................... | 600/532 |
| 2007/0093725 A1 * | 4/2007 | Shaw | ............................ | 600/543 |
| 2007/0256477 A1 * | 11/2007 | Moor | ........................... | 73/31.02 |
| 2008/0078232 A1 * | 4/2008 | Burke et al. | ................... | 73/23.3 |
| 2008/0097914 A1 * | 4/2008 | Dicks et al. | ................... | 705/50 |
| 2008/0183388 A1 * | 7/2008 | Goodrich | ...................... | 701/300 |
| 2008/0227466 A1 * | 9/2008 | Rabanne et al. | ........... | 455/456.1 |
| 2009/0085873 A1 * | 4/2009 | Betts et al. | .................... | 345/169 |
| 2009/0309711 A1 * | 12/2009 | Adappa et al. | ................ | 340/501 |

* cited by examiner

*Primary Examiner* — Jinsong Hu
*Assistant Examiner* — Nathan Taylor
(74) *Attorney, Agent, or Firm* — James Ray & Assoc

(57) ABSTRACT

The present invention in several embodiments is a cell phone with breath analyzer that can store a preprogrammed list of phone numbers that are not to be called once a person's blood alcohol level has reached a specific point. This device could look similar to traditional cell phones. Within the mouth piece, or other place on or in the phone is a blood alcohol detector. As a person talks/breaths into the phone, their blood alcohol level will be measured. If the level is over a predetermined amount, a previously programmed list of phone numbers cannot be accessed. This unit may also have the capability to store a help list for the user. This list would allow the consumer to easily call a specific list of individuals if they were in need of a ride or other forms of assistance.

18 Claims, 3 Drawing Sheets

CELL PHONE WITH BREATH ANALYZER

CROSS REFERENCE TO RELATED APPLICATION

This patent application is related to and claims priority from U.S. Provisional Patent Application Ser. No. 61/075,459 filed Jun. 25, 2008.

FIELD OF THE INVENTION

This invention generally pertains to mobile personal communication devices. More specifically, the present invention relates to a cellular phone with a breathalyzer and various functions related to these two integrated components.

BACKGROUND OF THE INVENTION

The invention is particularly applicable to cell phones with integrated breathalyzers for the detection of alcohol and more specifically ethanol. It is not uncommon for users of cell phones to drink to the point of intoxication and occasionally far beyond the point of intoxication, then proceed to make poor decisions after they are no longer capable of making reasonable choices. Worsening the situation is also the fact that many of these users once drunk don't remember what they did while they were drunk.

After drinking, people tend to want to reach out to others. Sometimes, the individuals they wish to reach are not appropriate to talk to when one's judgment may be impaired. People can often say things they normally wouldn't when they are under the influence of alcohol. A person may also need help but cannot clearly see whom they are calling. This could lead to embarrassing or even dangerous situations.

Accordingly, it has been considered desirable to develop a new and improved cellular phone which would overcome the foregoing difficulties and others while providing better and more advantageous overall results

SUMMARY OF THE INVENTION

The present invention in several embodiments is a cell phone with breath analyzer that can store a preprogrammed list of phone numbers that are not to be called once a person's blood alcohol level has reached a specific point. This device could look similar to traditional cell phones. Within the mouth piece, or other place on or in the phone is a blood alcohol detector. As a person talks/breaths into the phone, their blood alcohol level will be measured. If the level is over a predetermined amount, a previously programmed list of phone numbers cannot be accessed. This unit may also have the capability to store a help list for the user. This list would allow the consumer to easily call a specific list of individuals if they were in need of a ride or other forms of assistance. In several embodiments the phone may automatically call a predefined number for assistance if a high blood alcohol level or high breath alcohol level is measured. For example, the phone may be set to call a predetermined phone number if a BAC of 0.4 percent is measured or calculated. The phone could play a prerecorded message to the receiver of the phone number requesting help.

Additionally, the phone could be configured to work with an ignition interlock device to prevent the user from starting an interlocked car when the user's blood alcohol level is above a predetermined level. The predetermined level could be previously defined by the user or define in compliance with a court order or the like.

The blood alcohol sensor or alcohol sensor array could be any type known in the art, but preferably it is an ethanol specific fuel cell sensor. A silicon oxide sensor could also be used. In one embodiment the phone uses a combination of sensors comprising at least one ethanol specific fuel cell sensor and at least one silicon oxide sensor. In another embodiment multiple ethanol specific fuel cell sensors are used. In still another embodiment multiple silicon oxide sensors are used.

OBJECTS OF THE INVENTION

It is therefore one of the primary objects of the present invention to provide a mobile phone with a breathalyzer.

Another object of the present invention is to provide a mobile phone with a breathalyzer that is capable of blocking a set of predetermined phone numbers when a predetermined alcohol level is detected.

Still another object of the present invention is to provide mobile phone with a breathalyzer that is modified to work with an ignition interlock device to prevent an intoxicated user from driving the applicable vehicle.

In one embodiment the invention is a portable personal communication device comprising: at least one receiver, at least one transmitter, at least one antennae, at least one microelectronic processor, at least one sensor capable of detecting ethanol, wherein a signal from said at least one sensor capable of detecting ethanol is used by said portable personal communication device to calculate a blood alcohol content measurement. In another embodiment the blood alcohol content measurement is used by an ignition interlock system. In another embodiment the blood alcohol content measurement is used by a wireless ignition interlock system. In another embodiment the blood alcohol content measurement is used to block at least one phone number. In yet another embodiment the blood alcohol content measurement triggers a predetermined event. In still another embodiment the blood alcohol content measurement triggers the portable personal communication device to call a predetermined phone number. In yet still another embodiment the blood alcohol content measurement triggers the portable personal communication device to call a predetermined phone number with a prerecorded message. In still yet another embodiment said at least one sensor capable of detecting ethanol comprises a silicon oxide sensor. In still yet another embodiment said at least one sensor capable of detecting ethanol comprises an ethanol specific fuel cell sensor. In another embodiment the portable personal communication device further comprises at least one sensor capable of measuring temperature. In another embodiment the portable personal communication device further comprises at least one sensor capable of measuring temperature, wherein a signal from said at least one sensor capable of measuring temperature is used by said portable personal communication device to calculate said blood alcohol content measurement.

In yet another embodiment the invention is a portable personal communication device comprising: at least one receiver, at least one transmitter, at least one antennae, at least one microelectronic processor, at least one sensor capable of detecting ethanol, at least one sensor capable of measuring temperature, wherein a signal from said at least one sensor capable of detecting ethanol is used by said portable personal communication device to calculate a blood alcohol content measurement. In still another embodiment a signal from said at least one sensor capable of measuring temperature is used by said portable personal communication device to calculate said blood alcohol content measurement. In yet another embodiment the blood alcohol content measurement is used by an ignition interlock system. In still yet another embodiment the blood alcohol content measurement is used by a wireless ignition interlock system. In yet still another embodiment the blood alcohol content measurement is used to block at least one phone number. In another embodiment the blood alcohol content measurement triggers a predetermined event. In yet another embodiment the blood alcohol content measurement triggers the portable personal communication device to call a predetermined phone number. In still another embodiment the blood alcohol content measurement triggers the portable personal communication device to call a predetermined phone number with a prerecorded message.

In yet still another embodiment the invention is a portable personal communication device comprising: at least one receiver, at least one transmitter, at least one antennae, at least one microelectronic processor, at least one sensor capable of detecting ethanol, at least two sensors capable of measuring temperature, wherein a signal from said at least one sensor capable of detecting ethanol is used by said portable personal communication device to calculate a blood alcohol content measurement.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

Figure 1:
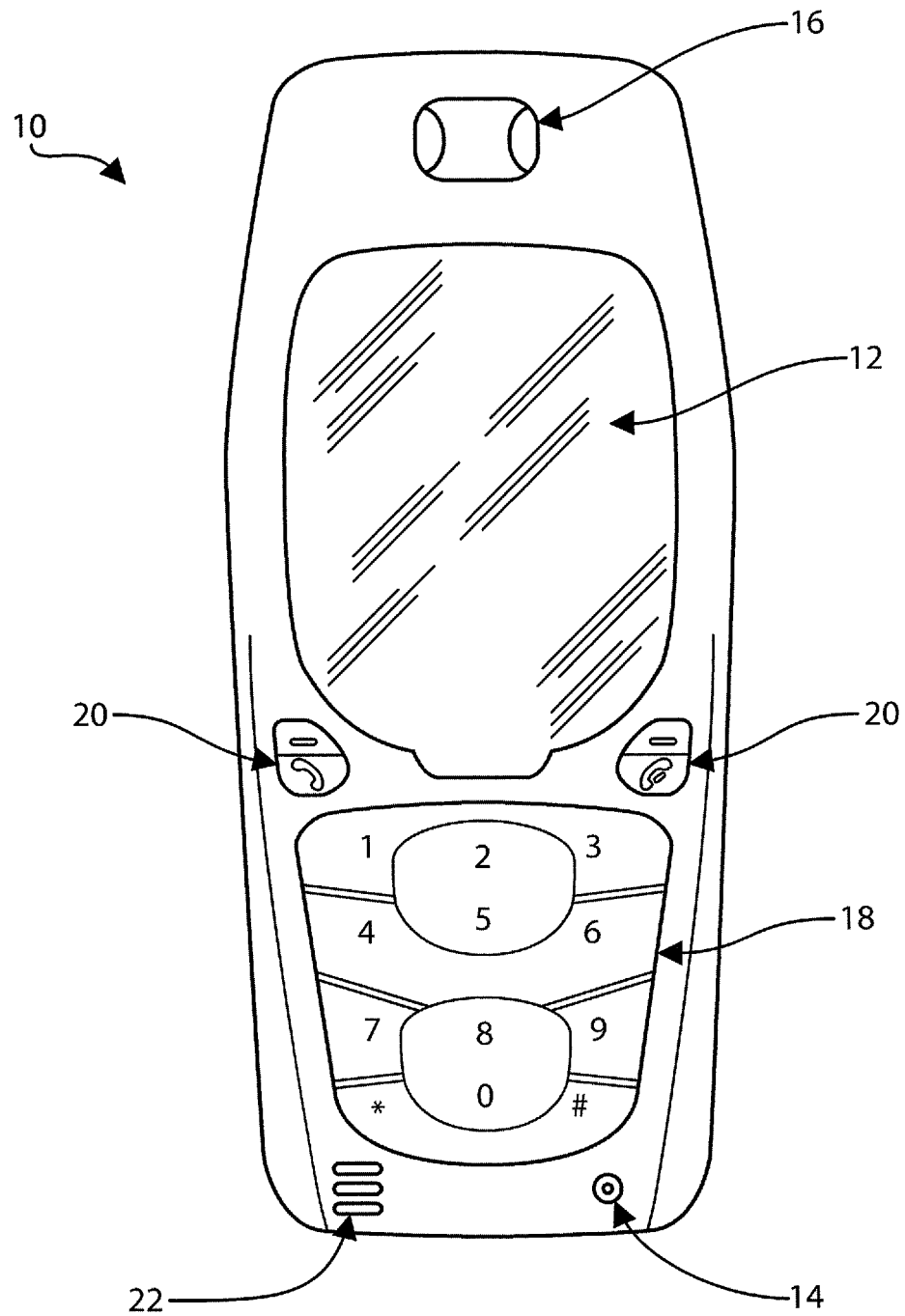
FIG. 1 is a general frontal view drawing of a preferred embodiment of the present invention.

BRIEF DESCRIPTION OF A PRESENTLY PREFERRED AND VARIOUS ALTERNATIVE EMBODIMENTS OF THE INVENTION

Prior to proceeding to the more detailed description of the present invention it should be noted that, for the sake of clarity and understanding, identical components which have identical functions have been identified with identical reference numerals throughout the several views illustrated in the drawing figures.

Reference is now made, more particularly, to FIG. 1 which is a general frontal view drawing of a preferred embodiment of the present invention. Phone 10 comprises display 12, microphone 14, speaker 16, keypad 18, function buttons 20 and alcohol detection unit 22. Alcohol detection unit 22 could be located anywhere on the phone, but in a preferred embodiment it is located proximally to microphone 14 so that alcohol in the users breath can be easily detected while the user talks on the phone 10. In a simple embodiment the alcohol detection unit comprises on alcohol sensor. In other more advanced embodiments the alcohol detection unit comprises an array of sensors, which could include silicon oxide sensors, ethanol specific fuel cell sensors, thermocouples, thermistors or the like. A thermocouple or themistor could be used to measure temperature which could be used to more accurately measure alcohol in the users breath. That is breathalyzers can be very sensitive to temperature, and will give false readings if not adjusted or recalibrated to account for ambient or surrounding air temperatures. The temperature of the subject is also very important. Therefore, it is advantageous to have multiple temperature sensors, thermocouples, thermistors or the like associated with the phone to measure ambient air temperature and/or measure the temperature of the user's breath to more accurately calculate blood alcohol content. An ambient air temperature sensor could be placed outside of alcohol detection unit 22, such ambient air temperature sensor could be placed with speaker 16. The user's temperature could also be calculated from a temperature sensor touching the user, such as on part of the phone that touches the user or the temperature of the user's breath could be used.

Figure 2:
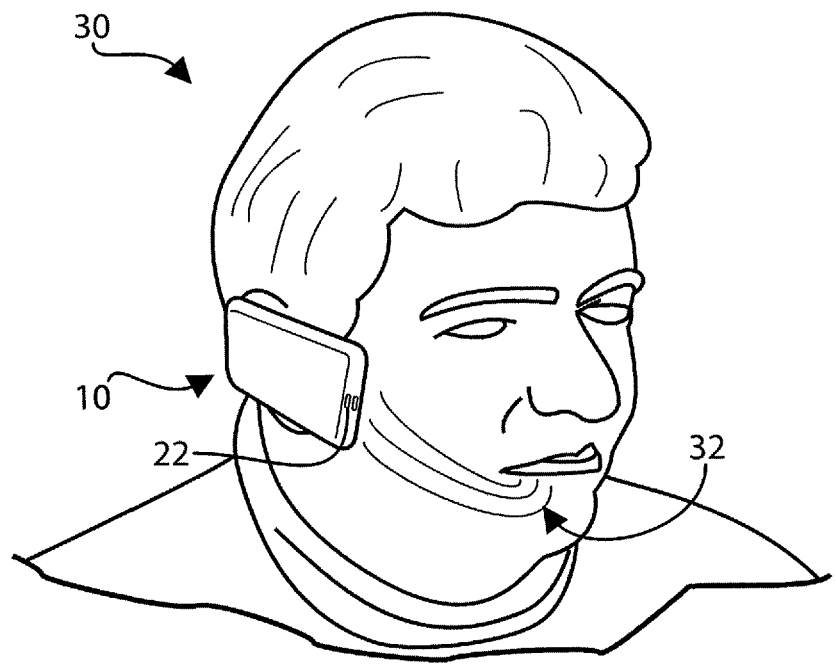
FIG. 2 is a general perspective drawing of a preferred embodiment of the present invention being used by a user.

Reference is now made, more particularly, to FIG. 2 which is a general perspective drawing of a preferred embodiment of the present invention being used by a user. Phone 10 is being used by user 30. In this embodiment user 30 is talking on phone 10 and user's breath 32 is moving past and/or through alcohol detection unit 22. Phone 10 could be configured to measure the alcohol content of user's breath 32 while user 30 is talking on phone 10. Optionally, this measurement could be used to block certain phone numbers if a certain predetermined limit is exceeded. There could be several groups of blockable phone numbers and each group could have a different predetermined limit. For example, if the user 30 has a low level of alcohol on his breath the phone 10 could block a group that includes his boss and potential employment contacts. If the user 30 has a higher level of alcohol on his breath the phone 10 could block a group that includes ex-girlfriends.

Figure 3:
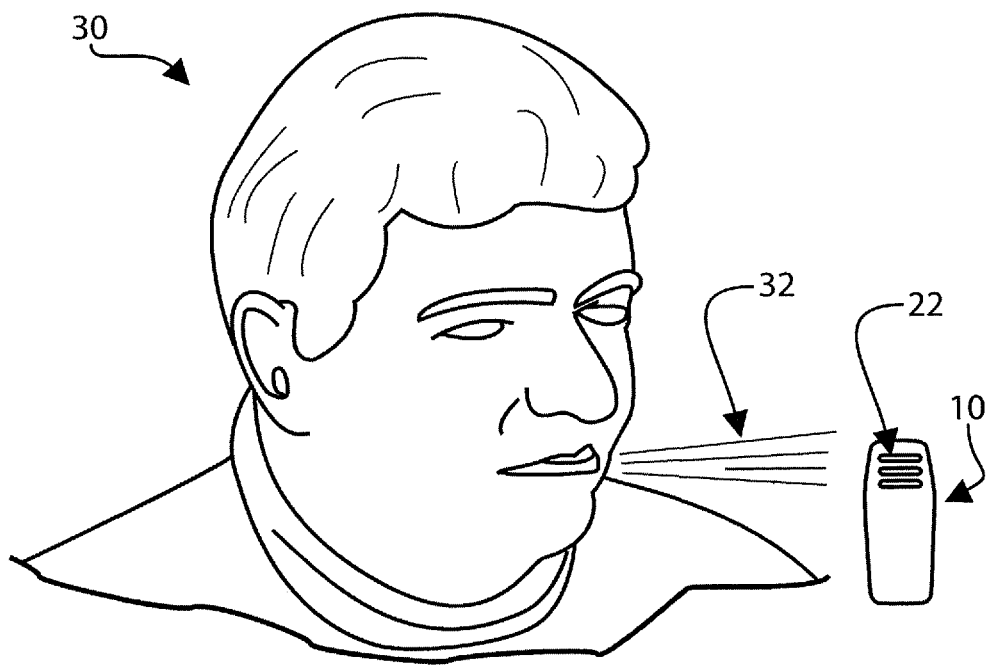
FIG. 3 is a perspective drawing of a preferred embodiment of the present invention being used by a user.

Reference is now made, more particularly, to FIG. 3 which is a perspective drawing of a preferred embodiment of the present invention being used by a user. Phone 10 is being used by user 30. In this embodiment user 30 is blowing into alcohol detection unit 22. Phone 10 could require user 30 to blow into alcohol detection unit 22 to unblock a blockable group or to pass an ignition interlock test. Additionally, the alcohol content of user's breath 32 could simply be displayed to user 30 on display 12 for his own information.

Figure 4:
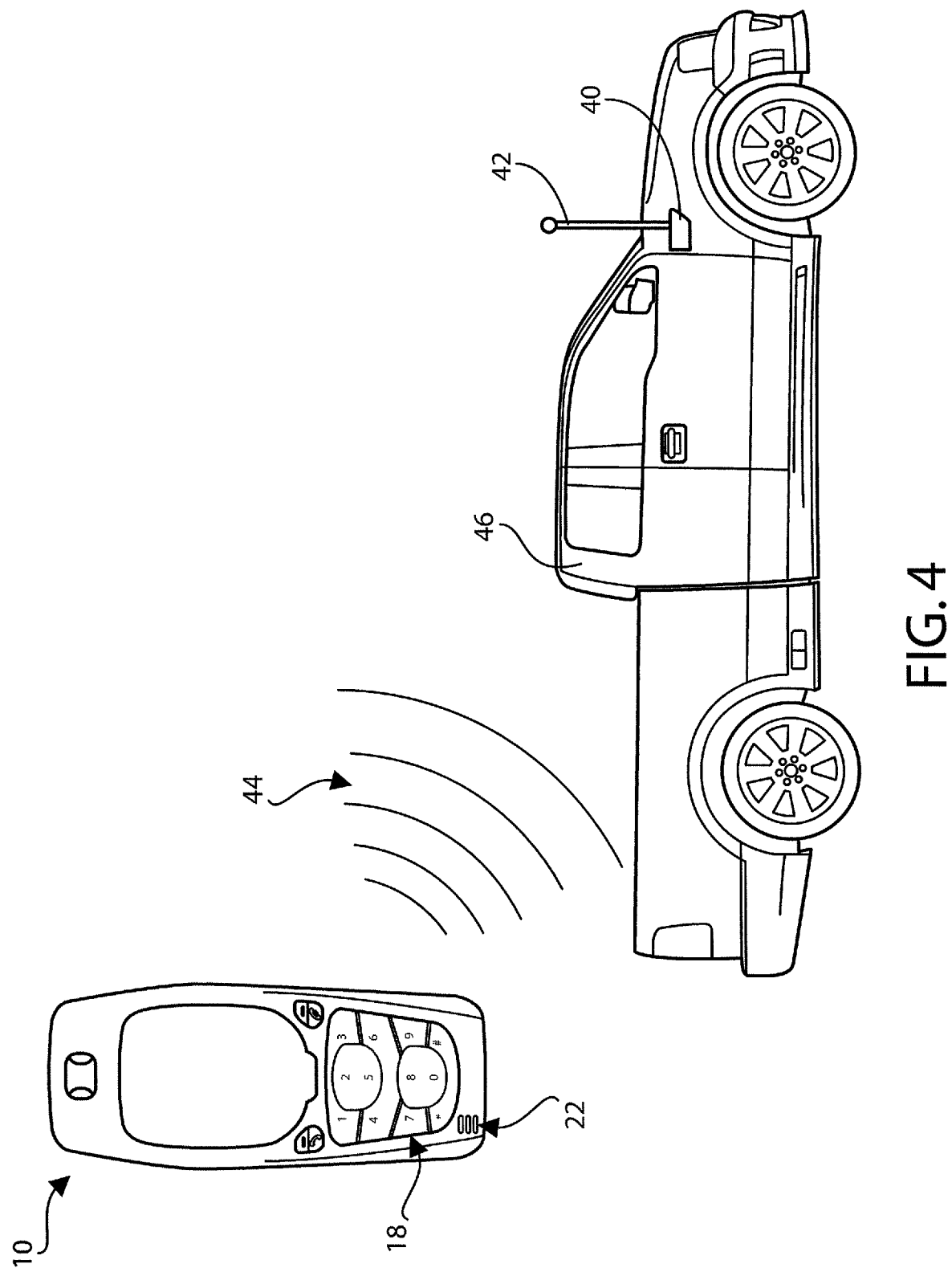
FIG. 4 is a schematic view of a preferred embodiment of the invention being used with a wireless capable ignition interlock system.

Reference is now made, more particularly, to FIG. 4 which is a schematic view of a preferred embodiment of the invention being used with a wireless capable ignition interlock system. Phone 10 comprising keypad 18 and alcohol detection unit 22, is used as a breathalyzer for wireless capable ignition interlock system 40. In a preferred embodiment wireless capable ignition interlock system 40 by means of antennae 42 would receive a radio frequency signal 44 from phone 10 indicating the user alcohol breath content. Radio frequency signal 44 is preferably a coded and secured signal. Radio frequency signal 44 could simply indicate whether user's alcohol breath content is low enough to drive or it could indicate the actual measurement of user's alcohol breath content. That is phone 10 or ignition interlock system 40 could determine whether user's alcohol breath content is low enough to allow the vehicle 46 to start and be driven. Additionally, phone 10 could be used as a breathalyzer for wireless capable ignition interlock system 40 during rolling retests as is typical with most ignition interlock systems.

While a presently preferred and various alternative embodiments of the present invention have been described in sufficient detail above to enable a person skilled in the relevant art to make and use the same it should be obvious that various other adaptations and modifications can be envisioned by those persons skilled in such art without departing from either the spirit of the invention or the scope of the appended claims.

What is claimed:

1. A portable personal communication device comprising:
a housing,
a microphone having an opening disposed on a front surface of said housing in close proximity to one edge thereof,
at least one receiver,
at least one transmitter,
at least one antennae,
at least one microelectronic processor,
at least one sensor having an opening disposed on said front surface of said housing in said close proximity to said one edge thereof and in a spaced relationship with said microphone, wherein said sensor and said microphone are further disposed adjacent opposite lateral edges of said housing and said at least one sensor configured to detect presence of ethanol,
wherein a signal from said at least one sensor configured to detect ethanol is used by said portable personal communication device to calculate a blood alcohol content measurement, and
whereby said portable personal communication device is configured to calculate said blood alcohol content measurement when a user of the portable personal communication device is speaking into said microphone.

2. The portable personal communication device of claim 1, wherein the blood alcohol content measurement is used by an ignition interlock system.

3. The portable personal communication device of claim 1, wherein the blood alcohol content measurement is used by a wireless ignition interlock system.

4. The portable personal communication device of claim 1, wherein the blood alcohol content measurement is used to block at least one phone number.

5. The portable personal communication device of claim 1, wherein the blood alcohol content measurement triggers a predetermined event.

6. The portable personal communication device of claim 1, wherein the blood alcohol content measurement triggers the portable personal communication device to call a predetermined phone number.

7. The portable personal communication device of claim 1, wherein the blood alcohol content measurement triggers the portable personal communication device to call a predetermined phone number with a prerecorded message.

8. The portable personal communication device of claim 1, wherein said at least one sensor capable of detecting ethanol comprises a silicon oxide sensor.

9. The portable personal communication device of claim 1, wherein said at least one sensor capable of detecting ethanol comprises an ethanol specific fuel cell sensor.

10. The portable personal communication device of claim 1, further comprising at least one sensor capable of measuring temperature.

11. The portable personal communication device of claim 1, further comprising at least one sensor capable of measuring temperature, wherein a signal from said at least one sensor capable of measuring temperature is used by said portable personal communication device, in combination with said at least one sensor configured to detect ethanol, to calculate said blood alcohol content measurement.

12. A portable personal communication device consisting of:
a housing,
a microphone disposed on a front surface of said housing in close proximity to one edge thereof,
a receiver,
a keypad disposed on said front surface of said housing,
a transmitter,
an antennae,
a microelectronic processor,
a sensor capable of detecting ethanol, wherein an opening to said sensor is disposed remotely from an opening to said microphone,
a sensor capable of measuring temperature, and
wherein the signals from said sensor capable of detecting ethanol and said sensor capable of measuring temperature are used by said portable personal communication device to calculate a blood alcohol content measurement.

13. The portable personal communication device of claim 12, wherein said opening to said sensor capable of detecting ethanol is disposed on said front surface of said housing in said close proximity to said one edge, and wherein said sensor and said microphone are disposed in a spaced apart relationship with each other adjacent opposite lateral edges of said housing.

14. The portable personal communication device of claim 13, wherein said opening to said at least one sensor capable of detecting ethanol is disposed on a rear surface of a housing of said portable personal communication device and said opening to said microphone is disposed on a front surface of said housing.

15. The portable personal communication device of claim 13, wherein said opening to said at least one sensor capable of detecting ethanol is disposed in an end surface of a housing of said portable personal communication device and said opening to said microphone is disposed on a front surface of said housing.

16. A portable personal communication device comprising:
at least one receiver,
at least one transmitter,
at least one antennae,
at least one microelectronic processor,
at least one sensor capable of detecting ethanol,
a microphone wherein an opening to said at least one sensor capable of detecting ethanol is disposed remotely from an opening to said microphone,
at least two sensors configured to measure temperature, wherein at least one of said at least two sensors is configured to measure ambient temperature and wherein at least another one of said at least two sensors is configured to measure temperature of person's breath, and
wherein a signal from said at least one sensor capable of detecting ethanol and said at least two sensors capable of measuring temperature are used by said portable personal communication device to calculate a blood alcohol content measurement.

17. The portable personal communication device of claim 13, wherein said opening to said at least one sensor capable of detecting ethanol and said opening to said microphone are disposed on a front surface of a housing of said portable personal communication device in a spaced apart relationship with each other and adjacent opposite lateral edges of said housing.

18. The portable personal communication device of claim 16, wherein said opening to said at least one sensor capable of detecting ethanol and said opening to said microphone are disposed on a front surface of a housing of said portable personal communication device in a spaced apart relationship with each other and adjacent opposite lateral edges of said housing.

\* \* \* \* \*